United States Patent
Sorge et al.

(10) Patent No.: US 6,261,797 B1
(45) Date of Patent: *Jul. 17, 2001

(54) PRIMER-MEDIATED POLYNUCLEOTIDE SYNTHESIS AND MANIPULATION TECHNIQUES

(75) Inventors: Joseph A. Sorge, Rancho Santa Fe; Kerstien A. Padgett, San Diego, both of CA (US)

(73) Assignee: Stratagene, La Jolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/713,404

(22) Filed: Sep. 13, 1996

Related U.S. Application Data

(63) Continuation-in-part of application No. 08/592,938, filed on Jan. 29, 1996, now abandoned.

(51) Int. Cl.[7] ............................ C12P 1/00; C12Q 1/68; C07K 14/00
(52) U.S. Cl. .................. 435/41; 435/6; 530/350
(58) Field of Search .................... 435/5, 6, 810, 435/41; 530/350; 536/23.1, 24.2, 24.3, 24.33

(56) References Cited

U.S. PATENT DOCUMENTS

| | | | |
|---|---|---|---|
| 4,942,227 | 7/1990 | Dervan et al. | 536/27 |
| 5,350,672 | * 9/1994 | Oberst et al. | 435/6 |
| 5,436,150 | 7/1995 | Chandrasegaran | 435/199 |
| 5,604,122 | * 2/1997 | Taylor | 435/172.3 |
| 5,683,869 | * 11/1997 | Ramsey-Shaw et al. | 435/6 |
| 5,691,140 | * 11/1997 | Noren et al. | 435/6 |

FOREIGN PATENT DOCUMENTS

WO90/06042 * 6/1990 (WO).

OTHER PUBLICATIONS

Scharf S., "Cloning with PCR", in PCR Protocols: A Guide to Methods and Applications, pp. 84–91, Editors: Innis et al., Academic Press, SanDiego, CA 1990.*

(List continued on next page.)

Primary Examiner—Ethan Whisenant
(74) Attorney, Agent, or Firm—Finnegan, Henderson, Farabow, Garrett & Dunner, L.L.P.

(57) ABSTRACT

The invention provides improved techniques for conveniently manipulating polynucleotides of interest without the need to rely upon the presence of naturally occurring restriction sites. Additionally, using the methods and primers of the invention, one may synthesize a polynucleotide of interest in a form which is easily and directionally cloned into a DNA sequence of choice without necessarily introducing extraneous nucleotides in the final polynucleotide product. The methods of the invention employ releasable primers that comprise a recognition site for a releasing enzyme joined to a region for annealing to the polynucleotide template of interest. Polynucleotide sequences of interest are synthesized using one or more synthesis primers, wherein at least one of the primers is a releasable primer. After synthesis, the synthesis product is cleaved by a releasing enzyme. In a preferred embodiment of the invention, inhibitory base analogs are incorporated in the synthesis product to protect against the formation of unwanted internal cleavage products. In another embodiment of the invention, at least one of the releasable primers is bound to an immobilizing solid phase support so as to produce immobilized synthesis products that may be conveniently released by a releasing enzyme. Another aspect of the invention is to provide releasable primers and kits for performing the subject methods. Typically, such kits may comprise a releasing enzyme and one or more reagents for performing a polynucleotide synthesis reaction, preferably a cyclic amplification reaction.

10 Claims, 2 Drawing Sheets

OTHER PUBLICATIONS

The New England Biolabs Catalog, p. 110 (1993/1994 Edition).*
The New England Biolabs Catalog, p. 31 (1993/1994 Edition).*
Berger, 1994, *Analytical Biochemistry* 222:1–8.
Kim et al., 1988, "Cleaving DNA At Any Predetermined Site With Adapters–Primers and Class–IIS Restriction Enzymes," *Science* 24:504–506.
Horton et al., *Gene* 77:61–68 (1989).
Lin and Schwartz, *Bio Techniques* 12:28–30 (1992).
Oakley et al., *Bioconjug. Chem.* 5:242–247 (1994).
Padgett et al., 1996, "Creating Seamless Junctions Independent Of Restriction Sites in PCR Cloning," *Gene*, 168(1):31–35.
Russek et al., *Cell Mol. Biol. Res.* 39:177–182 (1993).
Stillman et al., *PCR Methods and Applications* 3(6): 320–31 (1994).
Szybalski et al., *Gene* 100:13–26 (1991).
Weiner, M.P., *BioTechniques* 15:502–505 (1993).
Yon et al., *Nucl. Acids Res.* 17:4895 (1989).

* cited by examiner

US 6,261,797 B1

PRIMER-MEDIATED POLYNUCLEOTIDE SYNTHESIS AND MANIPULATION TECHNIQUES

CROSS REFERENCE TO RELATED APPLICATION

The present application is a continuation-in-part of U.S. application Ser. No. 08/592,938, filed Jan. 29, 1996, and now abandoned the disclosure of which is expressly incorporated by reference herein.

FIELD OF THE INVENTION

The invention is in the field of polynucleotide manipulation techniques, particularly amplification and cloning techniques.

BACKGROUND OF THE INVENTION

A significant problem with many of the currently available molecular biology techniques is their reliance upon naturally occurring convenient restriction sites. Modifications of the polymerase chain reaction (PCR) and other similar amplification techniques have been developed in an attempt to overcome this problem. In the absence of naturally occurring convenient restriction sites, it is possible to introduce restriction sites into the sequence of interest by using primers and PCR. However, this technique results in the presence of extraneous polynucleotides in the amplification products even after restriction digestion. Such extraneous polynucleotides can be problematic. For example, the introduction of unwanted nucleotides often imposes design limitations on the cloned product which may interfere with the structure and function of the desired gene products.

One method of joining DNA without introducing extraneous bases or relying on the presence of restriction sites is splice overlap extension (SOE). Yon et al., 1989, *Nucl. Acids Res.* 17:4895. Horton et al., 1989, *Gene* 77:61–68. This method is based on the hybridization of homologous 3' single-stranded overhangs to prime synthesis of DNA using each complementary strand as template. Although this technique can join fragments without introducing extraneous nucleotides (in other words, seamlessly), it does not permit the easy insertion of a DNA segment into a specific location when seamless junctions at both ends of the segment are required. Nor does this technique function to join fragments with a vector. Ligation with a vector must be subsequently performed by incorporating restriction sites onto the termini of the final SOE fragment. Finally, this technique is particularly awkward when trying to exchange polynucleotides encoding various domains or mutation sites between genetic constructs encoding related proteins.

Another commonly used genetic manipulation technique is immobilized amplification, e.g., immobilized PCR. In techniques involving immobilized PCR, i.e., bound PCR, polynucleotide amplification products are immobilized on a solid phase support. Immobilization is typically accomplished through the use of streptavidin (or avidin) and biotinylated polynucleotides, antibody-hapten binding interactions, or through the covalent attachment of nucleic acids to solid supports. A serious limitation, however, of such conventional immobilization techniques is that the amplification products cannot be conveniently unbound from the solid phase support for use in subsequent manipulations, e.g., sequencing of the amplification products.

An additional problem with conventional techniques, particularly the manipulation of amplification reaction products, is that cleavage at certain restriction sites must be avoided in order to obtain desired polynucleotides. Presently, however, this can only be accomplished by cumbersome techniques such as partial digestions and methylase protection.

Accordingly, in view of the foregoing limitations of current recombinant DNA technology, it is of interest to provide improved techniques for conveniently manipulating polynucleotides without having to rely on naturally occurring convenient restriction sites. It is also of interest to provide methods of synthesizing polynucleotides in which some or all of the nucleotides introduced through synthesis primers may be conveniently removed from the final synthesis product. Additionally, it is of interest to provide improved methods of manipulating polynucleotide synthesis products by restriction enzymes which overcome the problems of cleavage at internal sites within the synthesis products. Further, it is of interest to provide an improved method of releasing amplification products that are bound to a solid phase support. The present invention meets these needs.

SUMMARY OF THE INVENTION

The present invention relates to improved methods of synthesizing polynucleotides of interest. The invention is based, in part, on the use of enzymes, referred to herein as releasing enzymes, which cleave polynucleotide substrates. In one embodiment of the invention, it is preferred that the site cleaved by the releasing enzyme is different or distal from the enzyme recognition site on the substrate. The methods of the invention employ primers which comprise a recognition site for a releasing enzyme joined to a region for annealing to the polynucleotide template of interest. These primers are referred to as releasable primers. Preferably, the recognition site for the releasing enzyme is joined 5' to the annealing region.

In one embodiment of the invention, the releasable primers comprise a recognition site for a type IIS restriction endonuclease. The type IIS restriction endonuclease recognizes this site, but then cleaves the DNA in a sequence independent manner several base pairs 3' to the recognition site. Optionally, releasable primers of the invention comprise additional nucleotides located 5' and adjacent to the recognition site.

The releasable primers may be used for priming polynucleotide synthesis reactions, including, but not limited to, polymerase chain reactions and other amplification reactions.

The methods of the invention comprise the steps of synthesizing a polynucleotide sequence of interest with at least one releasable primer. The polynucleotide synthesis reaction may be, but is not necessarily, a cyclic amplification reaction. When polynucleotide synthesis occurs in a cyclic amplification reaction, the polymerase chain reaction (PCR) is particularly preferred for use. After synthesis, the synthesis product is cleaved by a releasing enzyme capable of recognizing the recognition site on the releasable primer. Restriction endonuclease inhibitory base analogs may be incorporated in the synthesis product to protect against unwanted cleavage of internal recognition sites by the releasing enzyme, yet still permit cleavage of the desired sites introduced by the releasable primer or primers.

In another embodiment of the invention, i.e., seamless domain replacement, a first synthesis product is produced using a pair of primers and a second synthesis product is produced using a second pair of primers, wherein at least one member of each pair of primers is a releasable primer. Both first and second synthesis products are subsequently cleaved by releasing enzymes. The resultant released first and second synthesis products may then be ligated to one another so as to produce a recombinant DNA construct that does not contain extraneous nucleotides introduced by the synthesis primers. This method may be used to conveniently replace one segment of a genetic construct with a similar (but different) segment of a second genetic construct.

In another embodiment of the invention, at least one releasable primer is bound to a solid phase support. After synthesis of a polynucleotide of interest using the bound primer, an immobilized synthesis product is produced. The immobilized synthesis product may be released by means of a releasing enzyme. Restriction endonuclease inhibitory base analogs may be incorporated in the synthesis product to protect against unwanted cleavage of internal restriction sites by the selected releasing enzyme, yet still permit cleavage of the desired restriction sites introduced by the releasable primer(s).

Another aspect of the invention is to provide releasable primers and kits for performing the subject methods. Typically, such kits comprise a releasing enzyme and one or more reagents for performing polynucleotide synthesis, e.g., a cyclic amplification reaction. Optionally, such kits further comprise nucleotide base analogs capable of inhibiting or substantially inhibiting cleavage by the releasing enzyme. Preferably, such inhibitory nucleotide base analogs are in the form of nucleoside triphosphates. The kits may also optionally comprise a polynucleotide primer comprising a recognition site for a releasing enzyme.

The methods of the invention permit one to efficiently synthesize and manipulate polynucleotides of interest by primer mediated polynucleotide synthesis, e.g., PCR, without introducing extraneous primer-derived nucleotides into the ultimate synthesis products, i.e., seamless polynucleotide synthesis. The invention allows the efficient directional cloning of a desired DNA sequence into any location without the limitation of naturally occurring convenient restriction sites. Additionally, the invention permits DNA synthesis products to be manipulated by restriction enzymes without problems of cleavage at undesired restriction sites.

DEFINITIONS

Figure 1:
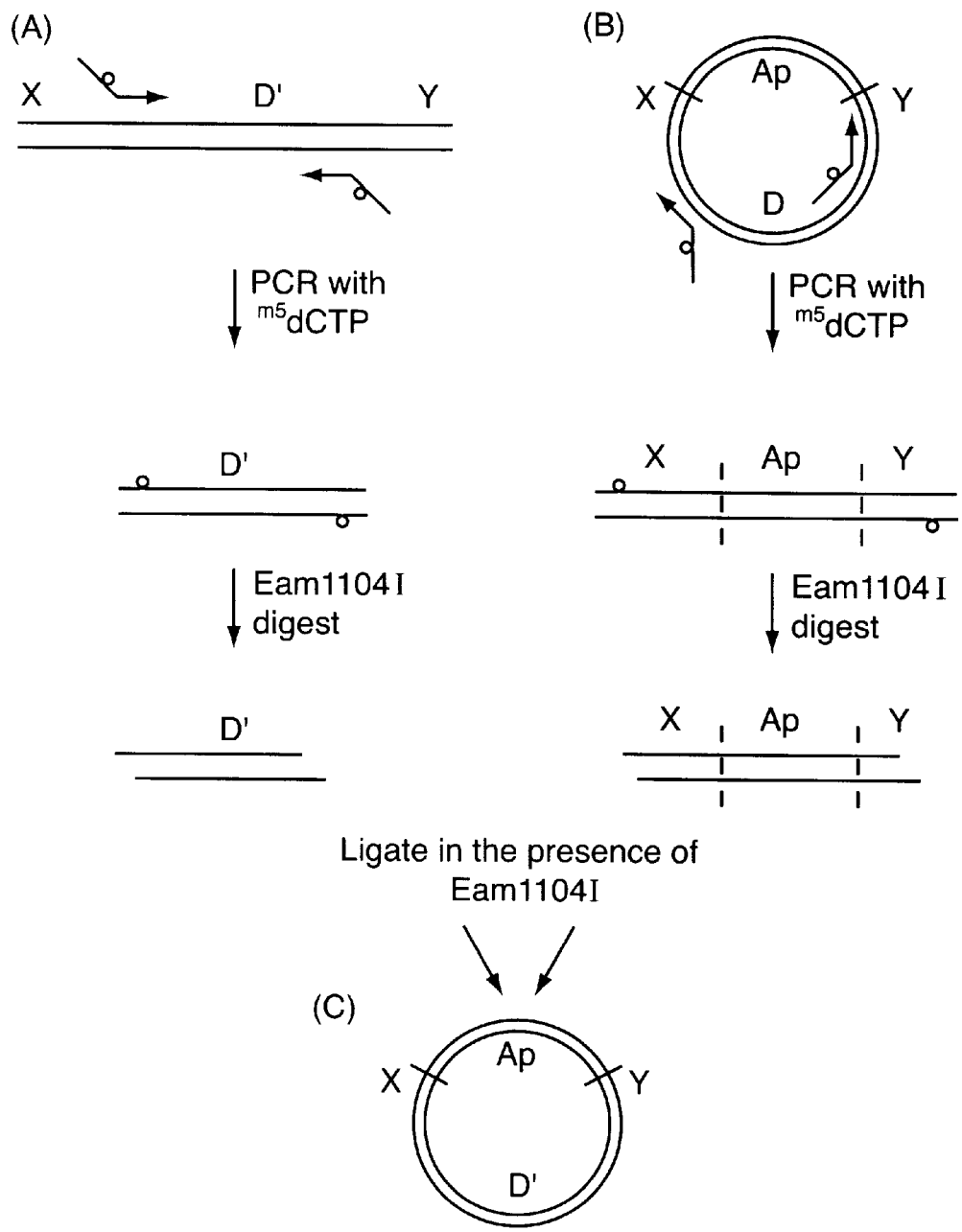
FIG. 1 is a schematic diagram of an embodiment of the invention in which two sets of releasable primers are used to produce two different synthesis products that are subsequently ligated to one another to produce a plasmid of interest. Part (A) of the figure shows a first polynucleotide synthesis product obtained by PCR. The figure shows the methods of the invention being employed to replace the D region on the plasmid in part (B) with the D' region on the plasmid of part (A). In part (A), PCR is performed with releasable primers in the presence of $^{m5}$dCTP (5-methyldCTP), thereby forming an amplification product. The amplification product is subsequently exposed to the releasing enzyme Eam1104I to produce a released synthesis product with overhanging, i.e., "sticky", non-identical non-palindromic ends to provide for directional cloning. The procedure shown in part (B) is essentially the same as in part (A) except different primers (with a different orientation) and a different template are used. In part (C), the two released synthesis products are ligated together in the presence of Eam1104I. The symbol • is used to indicate the Eam1104I recognition sequence CTCTTC.

The term "cyclic amplification reaction," as used herein, refers to a variety of enzyme mediated polynucleotide synthesis reactions that employ pairs of polynucleotide primers to amplify a given polynucleotide and proceed through one or more cycles, each cycle resulting in polynucleotide replication, i.e., synthesis. A cyclic amplification reaction cycle typically comprises the steps of denaturing the double-stranded template, annealing primers to the denatured template, and synthesizing polynucleotides from the primers. The cycle may be repeated several times so as to produce the desired amount of newly synthesized polynucleotide product. Guidance in performing the various steps of cyclic amplification reactions can be obtained from reviewing literature describing the polymerase chain reaction ("PCR") including, *PCR: A Practical Approach,* M. J. McPherson, et al., IRL Press (1991), PCR Protocols: *A Guide to Methods and Applications,* by Innis, et al., Academic Press (1990), and *PCR Technology: Principals and Applications of DNA Amplification,* H. A. Erlich, Stockton Press (1989). PCR is also described in numerous U.S. patents, including U.S. Pat. Nos. 4,683,195; 4,683,202; 4,800,159; 4,965,188; 4,889,818; 5,075,216; 5,079,352; 5,104,792, 5,023,171; 5,091,310; and 5,066,584, which are hereby incorporated by reference. Many variations of amplification techniques are known to the person of ordinary skill in the art of molecular biology. These variations include rapid amplification of cDNA ends (RACE-PCR), PLCR (a combination of polymerase chain reaction and ligase chain reaction), ligase chain reaction (LCR), self-sustained sequence replication (SSR), Q-beta phage amplification (as described in Shah et al., *Journal of Medical Micro.* 33(6): 1435–41 (1995)), strand displacement amplification, (SDA), splice overlap extension PCR (SOE-PCR), 3SR amplification (as described in Stillman et al., *PCR Methods and Applications* 3(6): 320–31 (1994), and the like. A person of ordinary skill in the art may use these known methods to design variations of the releasable primer mediated cyclic amplification reaction based methods explicitly described in this application.

The term "oligonucleotide," as used herein with respect to releasable primers, is intended to be construed broadly. Oligonucleotides include not only DNA but various analogs thereof. Such analogs may be, depending upon the specific releasing enzyme selected for use in a given embodiment of the invention, base analogs and/or backbone analogs, e.g., phosphorothioates, phosphonates, and the like. Techniques for the synthesis of oligonucleotides, e.g., through phosphoramidite chemistry, are well known to the person of ordinary skill in the art and are described, among other places, in *Oligonucleotides and Analogues: A Practical Approach,* ed. Eckstein, IRL Press, Oxford (1992). Preferably, the oligonucleotides used as releasable primers are DNA molecules.

The terms "amplification", "amplification products", "polynucleotide synthesis", and "polynucleotide synthesis products" are used herein as a matter of convenience and should not be interpreted to limit the subject invention to PCR or other cyclic amplification reactions. Accordingly, one skilled in the art having the benefit of this disclosure will appreciate that the present invention contemplates synthesis of end products through means other than PCR and related cyclic amplification reactions, e.g., DNA synthesis, DNA replication, cDNA synthesis, and the like.

DESCRIPTION OF THE SPECIFIC EMBODIMENTS

The present invention is based, in part, on the discovery that enzymes which cleave polynucleotides at a position which is different or distal from their recognition site may be used to clone or modify virtually any polynucleotide sequence independent of naturally occurring restriction sites. Accordingly, in certain embodiments of the invention, releasable primers are used to introduce recognition sites for enzymes which cleave polynucleotides at a site distinct from the recognition site. Particularly preferred are sites recognized by type IIS restriction endonucleases. When these primers are used to amplify a polynucleotide product, and then treated with type IIS restriction endonucleases, the polynucleotide sequences in the synthesis product which comprise the type IIS recognition sequence are completely or partially removed. Thus, using the methods of the invention, one may efficiently synthesize and manipulate polynucleotides of interest by primer mediated polynucleotide synthesis, e.g., PCR, without introducing some or all of the primer-derived nucleotides into the ultimate synthesis products.

The invention also allows directional cloning of a desired DNA sequence into any location. Additionally, the invention permits the treatment of polynucleotide synthesis products, including cyclic amplification reaction products, with releasing enzymes to produce the desired end products without cleaving internal restriction sites. The present invention also allows for the convenient release of polynucleotide synthesis products that are immobilized on solid phase supports.

In one specific embodiment of the invention described merely by way of illustrative example herein, the primers and methods of the invention are used to switch predetermined regions of a polynucleotide construct in a manner independent of any naturally occurring restriction sites. This method, referred to herein as "seamless domain replacement," affords the skilled practitioner unprecedented freedom to design, manipulate, and clone desired polynucleotide products.

Releasable Primers and Their Cognate Releasing Enzymes

In accordance with the embodiments of the invention, releasable primers and pairs of releasable primers, are provided. "Releasable primers" comprise a single stranded oligonucleotide and have two separate regions: (1) the "releasing enzyme recognition site" and (2) the "annealing region". In a preferred embodiment of the invention, the releasing enzyme recognition site is located 5' to the annealing region. The releasable primer may further comprise additional nucleotides located adjacent, preferably 5', to the releasing enzyme recognition site.

The "releasing enzyme recognition site" of a releasable primer may consist of the nucleotides which identify the recognition site for a given restriction endonuclease, in other words, a restriction endonuclease recognition site. In fact, the recognition site may be any site that is recognized by a sequence specific DNA binding protein. The recognition site may alternatively be a binding site for an "artificial restriction enzyme" which makes use of organic cleaving molecules such as those described in U.S. Pat. No. 4,942,227, issued Jul. 17, 1990. In certain embodiments of the invention, it is preferred that the "recognition site" is the recognition site for a restriction endonuclease wherein a base in one strand of the recognition site is lacking in the other strand of the recognition site. Such enzymes are defined herein for purposes of the invention as Class A enzymes (see infra). Alternatively, releasing enzyme recognition sites may be sites which are recognized by Class B or Class C enzymes. Class B and Class C enzymes are described more fully below in the next section.

In a preferred embodiment of the invention, the recognition site is recognized by a type IIS restriction endonuclease wherein one strand of the recognition sequence lacks a base that is present on the complementary strand of the recognition sequence. A type IIS restriction endonuclease is a restriction endonuclease that cleaves outside of the recognition site. A review of type IIS (also referred to as class IIS) restriction endonucleases can be found in Szybalski et al., *Gene* 100:13–26 (1991). In accordance with particularly preferred embodiments of the invention, the recognition site is for the type IIS restriction endonuclease Eam1104I. This recognition site is particularly preferred because it contains three cytosine residues in one strand which are lacking in the complementary strand of the recognition site.

Alternatively, the "releasing enzyme recognition site" of a releasable primer may consist of a protein or polypeptide (or biotin or other hapten) which is recognized by an enzyme capable of cleaving a polynucleotide substrate. In this case, the releasable primer will be a hybrid molecule comprised of protein (or biotin or other hapten) linked to a polynucleotide. The releasing enzyme recognizes the site on the protein portion of the releasable primer, and then cleaves the polynucleotide portion of the releasable primer. The cleavage may be performed by a catalytic protein domain of the releasing enzyme, or may be performed by an organic cleaving moiety linked to the releasing enzyme. In embodiments of the invention in which the hybrid molecules are comprised of biotin or other haptens, the releasing enzyme will recognize the biotin or hapten portion of the hybrid molecule.

The "annealing region" of a releasable primer of the invention comprises a polynucleotide sequence designed to anneal to target polynucleotides and prime synthesis of a desired polynucleotide at a specific location on a polynucleotide template. Polynucleotide synthesis products produced in a synthesis reaction employing a releasable primer may be contacted with a releasing enzyme that cleaves within the recognition site of the releasable primer or outside the recognition site (when the releasing enzyme is a type IIS restriction endonuclease). The precise nucleotide sequence of the annealing region in a specific embodiment of the invention is dependent upon the nucleotide sequence to which the releasable primer is designed to anneal.

Principles for designing amplification primers that anneal to and amplify polynucleotides of interest are well known to the person of ordinary skill in the art and may be readily applied for use in the design of annealing regions of the releasable primers of the invention. The annealing region hybridizes to templates for synthesis in a manner essentially identical to the annealing of primers in conventional PCR. The annealing region should be of sufficient length to permit specific annealing to the targeted sites. Preferably, the annealing region is at least nucleotides in length, more preferably, at least 20 nucleotides in length. While the annealing region may be 30 nucleotides in length or significantly longer, the increased length is usually not necessary to produce the desired synthesis products. Additionally, a releasable primer with a long annealing region, i.e., greater than about 30 nucleotides, may be unnecessarily difficult and expensive to synthesize.

In certain embodiments of the invention, it may be of interest to provide portions of the annealing region that do not necessarily anneal to the target template, thereby providing for the introduction of additional polynucleotide sequences into the synthesis product. These additional nucleotides may be used to introduce site-directed mutations or to facilitate additional sequence manipulations.

Releasable primers may further comprise additional nucleotides located 5' and adjacent to the recognition site. These additional nucleotides are optionally present in releasable primers of the invention. Such additional nucleotides located 5' to the recognition site may enhance the activity of the selected releasing enzyme. Preferably, the additional 5' nucleotides are of minimal length to reduce the possibility of hybridization to non-targeted polynucleotide sequences. Nucleotide sequence information of a polynucleotide comprising the target sequence for synthesis may be used in designing the sequence of any additional nucleotides located 5' to the recognition site so that the releasable primers do not anneal to non-targeted segments of the polynucleotide for synthesis or self-anneal to segments of the primer. In those embodiments of the invention in which the releasing enzyme is Eam1104I, preferably at least two additional nucleotides are present 5' to the Eam1104I recognition site. Another aspect of the present invention is the discovery that these two or more additional nucleotides significantly improves Eam1104I activity.

"Releasing enzymes" are enzymes which are capable of cleaving polynucleotide substrates at desired sites introduced by the releasable primer or primers of the invention and, when used in accordance with methods of the invention, are either incapable of or may be rendered incapable of undesired cleavage at internal sites. Releasing enzymes useful in the present invention are restriction endonucleases capable of recognizing the releasing enzyme recognition site introduced by a given releasable primer. Releasing enzymes may be naturally occurring restriction enzymes, or may be hybrid molecules comprised of a polynucleotide binding domain attached to a cleaving domain. For example, releasing enzymes may include hybrid enzymes such as those described in U.S. Pat. No. 5,436,150, issued Jul. 25, 1995, wherein the cleavage domain of the Fok I enzyme is linked to the recognition domain of another protein. Additionally, the recognition domain of the releasing enzyme may be linked to a non-protein cleaving agent, for example, an organic DNA cleaving moiety, such those described by Oakley et al. (1994), Bioconjug. Chem. 5:242–247. Further, the releasing enzyme may be an "artificial restriction enzyme" similar to those described in U.S. Pat. No. 4,942,227, issued Jul. 17, 1990.

In preferred embodiments of the invention, the releasing enzyme is a type IIS restriction endonuclease wherein the type IIS endonuclease may also be further characterized as a Class A, B or C enzyme (as defined herein infra.). Type IIS restriction endonucleases of interest recognize a specific nucleotide sequence and catalyze a double-stranded cleavage in a region outside the specific sequence of the restriction endonuclease recognition site. By using type IIS restriction endonucleases as releasing enzymes, all or part of the nucleotides introduced by the releasable primers of the invention may be removed from the polynucleotide product.

Preferred type IIS restriction endonucleases for use as releasing enzymes cleave DNA 3' with respect to the recognition site. The type IIS restriction endonuclease Eam1104I has been found particularly useful in the methods of the invention, and its use is specifically described by way of example herein. Many different type IIS restriction endonucleases and other restriction endonucleases are known to the person of ordinary skill in art, for example, see Szybalski, et al., Gene 100:13–26 (1991); and Ausubel, et al., Current Protocols in Molecular Biology, John Wiley & Sons (1995). It will be further appreciated by a person of ordinary skill in the art that new restriction endonucleases are continually being discovered and may be readily adapted for use in the subject invention.

Releasing enzymes may also include enzymes which cleave polynucleotides but which recognize a site which is other than a polynucleotide sequence, for example, another protein. Examples of such releasing enzymes are, for example, exonucleases and polymerases having exonuclease activity.

In one embodiment of the invention, a polynucleotide of interest is synthesized in a polynucleotide synthesis reaction employing a primer that is a releasable primer. The polynucleotide synthesis reaction may be, but is not necessarily, a cyclic amplification reaction. In those embodiments of the invention in which synthesis occurs in a cyclic amplification reaction, typically 10–30 amplification cycles are used; however, the number of cycles may be as low as 1. Amplification reaction parameters, e.g., temperature and time, may be determined by reference to conventional cyclic amplification techniques such as the polymerase chain reaction (PCR). In a cyclic amplification reaction employing a pair of primers, at least one of the primers is a releasable primer. In a preferred embodiment of the invention, the first and second primers of a cyclic amplification reaction are both releasable primers.

In accordance with the invention, the polynucleotide synthesis reaction of the invention results in the generation of a polynucleotide synthesis product, i.e., a double-stranded polynucleotide, which incorporates at least one releasable primer. After the desired synthesis product is produced, the synthesis product is contacted with a releasing enzyme. The releasing enzyme cleaves the synthesis product according to the sites introduced by the releasable primer during the synthesis reaction, whereby a released synthesis product is produced. Releasing enzymes that are type IIS restriction endonucleases, and thus cleave outside the releasing enzyme recognition site, may be used to produce released synthesis products that do not contain either all or part of the nucleotide sequences derived from the releasable primer or primers used to generate the polynucleotide synthesis product. Pairs of releasable primers may be used to produce released polynucleotide synthesis products that have non-identical overhanging ends, thereby permitting directional cloning of the released polynucleotide synthesis product in a predetermined orientation.

Preventing Cleavage at Internal Sites

Treatment of synthesis products with releasing enzymes may result in the formation of undesired digestion products because of the presence of "internal", i.e., pre-existing, restriction sites in regions of the synthesis products not derived from the synthesis primers. These internal restriction sites may be identified prior to synthesis or may be cryptic because no prior sequence information exists about the entire polynucleotide being synthesized.

This potential problem with internal restriction sites can be avoided by incorporating inhibitory base analogs into the polynucleotide synthesis products to protect or substantially protect the internal restriction sites from cleavage by the releasing enzyme. In accordance with an aspect of the invention, protection of internal restriction sites is accomplished by selection of a releasing enzyme that is an analog sensitive releasing enzyme with respect to the nucleotide base analog or analogs selected for use.

Analog sensitive releasing enzymes are releasing enzymes that are inhibited or substantially inhibited by a base analog at a nucleotide or nucleotides of the recognition site and/or the cleavage site of the restriction endonuclease. It will be appreciated by those skilled in the art that a given analog sensitive releasing enzyme is not inhibited or substantially inhibited by all nucleotide base analogs.

Accordingly a given releasing enzyme is analog sensitive with respect to a given nucleotide base analog. Conversely, a nucleotide base analog that inhibits or substantially inhibits the releasing enzyme is an inhibitory base analog with respect to that releasing enzyme. An example of an analog sensitive releasing enzyme is Eam1104I, which is inhibited by 5-methylcytosine (5-methyl-dCTP) at the recognition site, i.e., 5-methylcytosine is an inhibitory base analog with respect to Eam1104I.

Synthesis of a polynucleotide of interest with inhibitory base analogs may be accomplished by performing a polymerase mediated polynucleotide synthesis reaction with a nucleoside triphosphate mixture comprising the four basic nucleoside triphosphates (deoxyadenosine triphosphate, deoxyguanosine triphosphate, deoxycytidine triphosphate, and deoxythymidine triphosphate) or functional equivalents thereof, wherein at least one of the four basic nucleoside triphosphates is modified to comprise an inhibitory base analog rather than a conventional, i.e., non-inhibiting, nucleotide.

Examples of inhibitory base analogs include 6-methyladenine, 5-methylcytosine, 5-hydroxymethylcytosine, and the like. Inhibitory base analogs may be in the form of deoxyribonucleotide triphosphates (or functional equivalents thereof), in order to provide for polymerase mediated incorporation. Inhibitory nucleotide analogs may also be alpha-thio-deoxyribonucleotide triphosphate analogs. The present invention contemplates the use of any of a multitude of possible nucleotide base analogs as inhibitory base analogs, including, but not limited to, 2'-deoxyriboinosine, 5-iodo-2'-deoxyribocytosine, 5-mecuri-2'-deoxyriboguanosine. Accordingly, those skilled in the art will appreciate that alternative nucleotide base analogs may be suitably utilized as inhibitory base analogs in the invention, provided that such analogs are capable of being specifically incorporated within and protecting or substantially protecting double stranded DNA from cleavage by the selected releasing enzyme. It will also be readily appreciated by persons skilled in the art that in addition to the use of base analogs, analogs of phosphorylated sugars, e.g., phosphorothioates may be used to inhibit releasing enzyme activity. In a preferred embodiment of the invention, the inhibitory base analog is a methylated base analog, and the releasing enzyme is a methylation sensitive releasing enzyme.

The choice of a particular inhibitory base analog or analogs for use in a given embodiment of the invention is dependent upon the particular releasing enzyme selected for use. Certain releasing enzymes for use in the subject methods are inhibited or substantially inhibited by inhibitory base analogs in the recognition site of the restriction endonuclease. The term "substantially inhibited" is used to indicate that the inhibition of the enzymatic activity need not be complete. In many embodiments of the invention, the level of inhibition may be significantly less than complete inhibition because only partial inhibition is necessary to produce a useful amount of the ultimately desired released synthesis product. Inhibition of releasing enzyme cleavage may be achieved by incorporation of the inhibitory base analog into the recognition site and/or the restriction endonuclease cleavage site (when the recognition site and cleavage site are separate from one another).

The inhibitory effects of several nucleotide base analogs (particularly, naturally occurring methylated bases) on the activity of many restriction endonucleases is well described in the literature of molecular biology (see for example, Ausubel et al., *Protocols in Molecular Biology*, John Wiley & Sons (1995)). However, it may be necessary to determine whether or not a given nucleotide base analog is an inhibitory base analog with respect to a given restriction endonuclease. The determination of whether or not a given nucleotide base analog is inhibitory with respect to a given releasing enzyme may be made by techniques well known to a person of ordinary skill in the art. For example, a polynucleotide known to be cleaved by a given releasing enzyme can be synthesized with a nucleotide base analog of interest using conventional enzymatic or chemical polynucleotide synthesis techniques. After synthesis, the polynucleotide is treated, i.e., digested, with a restriction endonuclease for potential use as a releasing enzyme which cleaves at the anticipated cleavage sites. The results of the digestion are then analyzed by gel electrophoresis (or the functional equivalent thereof) in order to determine if the anticipated digestion products are produced.

Additionally, the choice of an inhibitory base analog for use in a given embodiment of the invention will in part be determined by the sequence of the restriction endonuclease recognition site and the annealing region. The relationship of such sequences to the nucleotide base analog inhibition sensitivities of the releasing enzyme is an important factor in selecting the nucleotide base analog or analogs for use in a given embodiment of the invention. This relationship is of particular importance for purposes of the present invention because the inhibitory base analogs selected for use should not significantly interfere with the ability of the selected releasing enzyme to cleave at either the recognition site or a cleavage site within the annealing region of the releasable primer or primers. If inhibitory base analogs incorporated into the synthesis products at locations complementary to the releasable primer significantly inhibit cleavage, then the synthesis products will not be converted into the desired released synthesis products by the releasing enzyme.

In accordance with the invention, alternative approaches may be used to avoid potential inhibition of released synthesis product formation. One way is to select a releasing enzyme having a recognition sequence that is asymmetric, wherein one strand of the recognition sequence lacks a base that is present on the complementary strand of the recognition sequence, and modification of that base inhibits the activity of the enzyme. These types of enzymes are referred to herein as Class A enzymes. An example of such a Class A releasing enzyme and inhibitory base analog combination is Eam1104I (having a recognition site 5'-CTCTTC-3') and 5-methylcytosine (or other cytosine derived inhibitory analogs). Because cytosine does not base pair with the cytosine or thymine of the recognition site of the releasable primer, 5-methylcytosine cannot be incorporated into the complementary strand of the Eam1104I recognition site of the releasable primer. Thus, 5-methylcytosine cannot interfere with the ability of Eam1104I to produce released synthesis products. Therefore, when the releasing enzyme used in the subject methods is the particularly preferred Eam1104I, 5-methylcytosine may be used as the inhibitory base analog.

The problem of potential inhibition of released synthesis product formation may also be avoided by using a releasing enzyme that cleaves when the recognition site of the enzyme has the selected inhibitory base analog in one strand, but is inhibited when the inhibitory base analog is present in both strands of the recognition site. In this embodiment of the invention, the restriction site may be identical and symmetric on both strands, or may be asymmetric. These enzymes, which are inhibited only when both strands contain the inhibitory base analog, are referred to as Class B enzymes. The desired nucleotide product is synthesized using an appropriate inhibitory base analog and the releasable primer (which does not itself contain an inhibitory base analog). Since the recognition sequence in the releasable primer incorporates inhibitory base analog in only one strand (the synthesized complementary strand), the releasing enzyme will cleave at the primer sequence.

Yet another way to allow for the release of synthesis product formation, while avoiding cleavage at internal sites, is by utilizing a primer which lacks inhibitory base analogs, and incorporating inhibitory base analogs into polynucleotide strands primed by the releasable primer but not incorporating the inhibitory analogs into the strand complementary to the releasable primer. The resultant polynucleotide does not have an inhibitory base analog in either strand of the recognition site introduced by the releasable primer. These polynucleotides may then be treated with a releasing enzyme that is inhibited by inhibitory base analogs incorporated into either one or both strands of a restriction site. These types of releasing enzymes are referred to as Class C enzymes. The releasing enzyme may have a symmetric recognition site or an asymmetric site.

Figure 2:
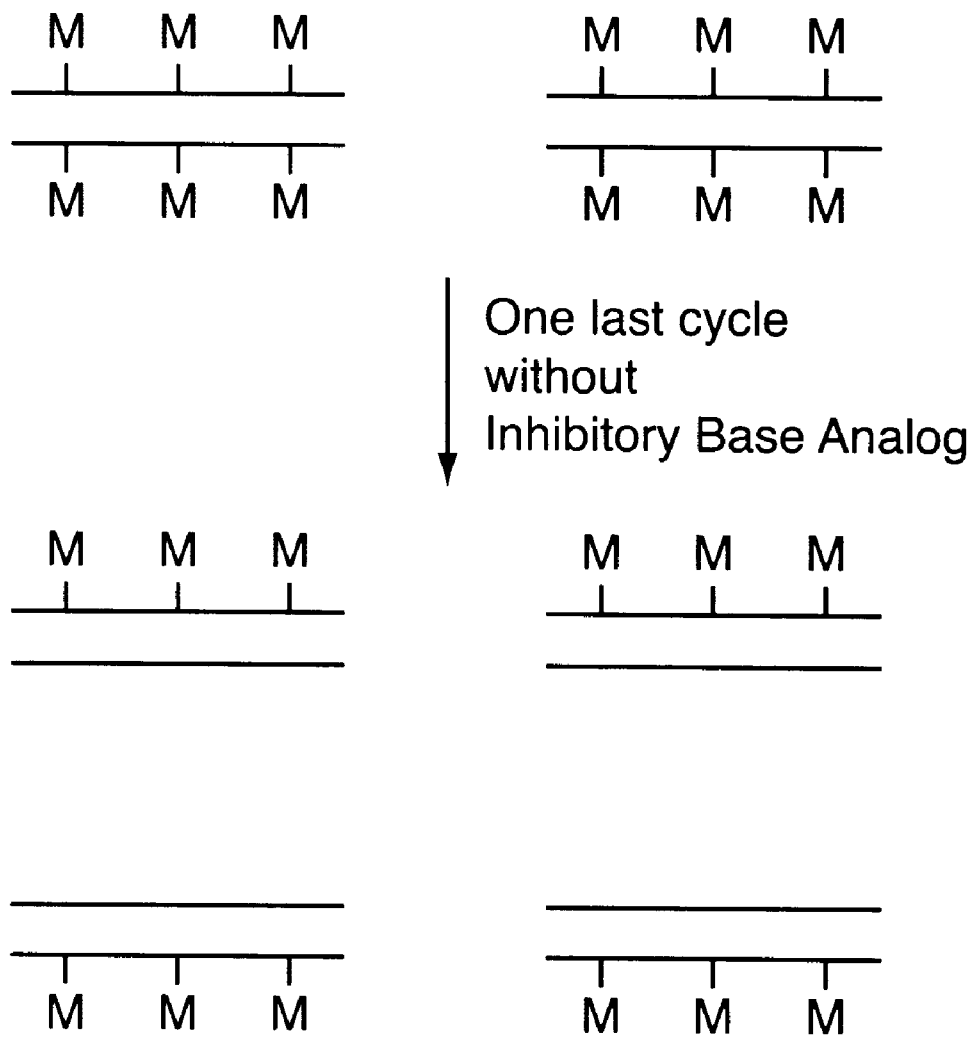
FIG. 2 is a schematic representation of cycles within a PCR reaction. The diagram indicates that PCR is performed in the presence of an inhibitory base analog. The last cycle of PCR is performed in the absence of the inhibitory base analog. "M" represents the inhibitory base analog, i.e., a modified base. The products of the last cycle only have inhibitory base analogs in one strand.

One method of producing polynucleotide synthesis products that have inhibitory base analogs in only one strand of the internal recognition sites is through cyclic amplification reactions (see FIG. 2). Inhibitory base analogs may be present during initial reaction cycles of the cyclic amplification reaction, but omitted from the last synthesis step. A purification reaction to remove unincorporated inhibitory base analogs may be performed prior to this last synthesis step, thereby increasing the yield of the desired hemimodified polynucleotide synthesis product.

Enzymes that may be used to catalyze polynucleotide synthesis in the synthesis steps of the invention, including cyclic amplification reactions, are well known to the person skilled in the art and include, but are not limited to, Taq DNA polymerase, Pfu DNA polymerase (Stratagene), phage T7 polymerase, phage T4 polymerase, *E. coli* DNA polymerase I, Vent™ (New England Biolabs, Beverly Mass.) DNA polymerase, Deep Vent™ DNA polymerase (New England Biolabs, Beverly Mass.), Moloney Murine Leukemia Virus reverse transcriptase, and the like. In those embodiments of the invention in which polynucleotide synthesis is achieved by means of a cyclic amplification reaction, the enzyme used to catalyze the polynucleotide synthesis reaction is preferably a thermostable DNA polymerase.

When the DNA sequence for synthesis is relatively long and synthesis is achieved by means of a cyclic amplification reaction, it may be desirable to use a mixture of thermostable DNA polymerases, wherein one of the DNA polymerases has 5'-3' exonuclease activity and the other DNA polymerase lacks or substantially lacks 5'-3' exonuclease activity. A description of how to amplify long regions of DNA using these polymerase mixtures can be found, among other places, in U.S. Pat. No. 5,436,149, Cheng et al., *Proc. Natl. Aca. Sci. USA* 91:5695–9 (1994), and Barnes *Proc. Natl. Aca. Sci. USA* 91:2216–2220 (1994) and U.S. patent application Ser. Nos. 08/164,290, and 08/197,791.

Seamless Domain Replacement

The invention is particularly useful because it may be applied to the convenient switching of polynucleotide sequences in related genetic constructs either with or without the introduction of additional nucleotides. This embodiment of the invention is referred to herein as "seamless domain replacement." Seamless domain replacement involves the use of seamless synthesis reactions to produce a polynucleotide of interest by synthesizing two different polynucleotide sequences using separate sets of primers, cleaving the synthesis products with a releasing enzyme, and ligating together the two sets of released synthesis products. Either all the primers in the two synthesis reactions are releasable primers or one of the primers in each of the two synthesis reactions is a releasable primer. In a preferred embodiment of the invention, all of the primers used for seamless domain replacement are releasable primers. In a particularly preferred embodiment of the invention, which may be used to prevent the introduction of extraneous nucleotides, the releasing enzyme recognition sites of the releasable primers are sites for type IIS restriction endonucleases. The primers may be selected so as to produce released polynucleotide synthesis products that have non-identical overhanging ends, thereby permitting directional cloning.

An example of an embodiment of seamless domain replacement can be found in FIG. 1. FIG. 1 is a schematic diagram of seamless domain replacement showing a first (A) and a second (B) cyclic amplification reaction using releasable primers. The embodiment of the method of the invention shown in FIG. 1 results in the replacement of polynucleotide sequence D with polynucleotide sequence D'. This replacement method comprises the following steps: a polynucleotide of interest is amplified using first and second releasable primers, thereby producing a first synthesis product. The first synthesis product is then treated, i.e., contacted, with a releasing enzyme to produce a first released synthesis product. The method further comprises the step of performing a second cyclic amplification reaction using third and fourth releasable primers to produce a second synthesis product. The second synthesis product is then treated with a selected releasing enzyme to produce a second released synthesis product. The first and second released synthesis products may then be ligated together to produce the genetic construct of interest. Performing the ligation step in the presence of the releasing enzyme reduces the time and steps required to obtain the desired product.

The method of the invention can be used to directionally clone any synthesis product by designing the releasable primers such that the releasing enzyme or enzymes produce non-identical sticky ends (i.e., overhanging ends as opposed to blunt ends). Thus, to directionally clone the seamless domain replacement shown in FIG. 1, the released synthesis products produced by the first and second releasable primers produce a first released synthesis product having non-identical non-palindromic sticky ends that are ligatable (in a directed orientation) with the sticky ends of the second released synthesis product produced from the third and fourth releasable primers.

Another aspect of the invention is to provide releasable primer sets suitable for carrying out seamless domain replacement methods of the invention. The subject primer sets comprise (1) a first primer pair consisting of first and second releasable primers and (2) a second primer pair consisting of third and fourth releasable primers. The releasing enzyme recognition sites of all members of a set of releasable primers for seamless domain replacement may be identical. The annealing regions of the releasable primers are selected subject to the following constraints: (1) a first released synthesis product, resulting from treatment of the synthesis product by a releasing enzyme, has two non-identical sticky ends, (2) a second released synthesis product, resulting from treatment of the synthesis product by a releasing enzyme, has two non-identical sticky ends that are homologous, i.e., capable of being ligated, to the two non-identical sticky ends of the first released synthesis product.

Use of the Invention To Release Polynucleotides from Solid Supports

The present invention is also directed to methods for the convenient release of synthesis products bound or immobilized on a solid support. Performing cyclic amplification reactions so as to produce a bound, i.e., immobilized, synthesis product has numerous applications, particularly in the field of assays for a polynucleotide of interest. Such assays may have diagnostics applications for the detection of microorganisms or indicia of disease. Furthermore, cyclic amplification reactions that produce an immobilized synthesis product, particularly a releasable synthesis product, may readily be adapted for use with automated equipment.

Polynucleotide synthesis products may be produced in a form attached to solid phase supports by employing the subject methods of synthesis, wherein polynucleotide synthesis is primed by at least one releasable primer attached to a solid phase support. The releasable primer may be attached to the solid phase support by any of a variety of means, including covalent and non-covalent bonds. Methods for the attachment of polynucleotides to solid supports are well known to the person of ordinary skill in the art. Descriptions of methods for attachment of nucleic acids to a variety of solid supports can be found, among other places, as follows: nitrocellulose (Ranki et al., *Gene* 21:77–85 (1983), cellulose (Goldkorn and Prockop, *Nucl. Acids Res.* 14:9171–9191 (1986), polystyrene (Ruth et al., *Conference of Therapeutic and Diagnostic Applications of Synthetic Nucleic Acids, Cambridge U.K.* (1987), teflon-acrylamide (Duncan et al. *Anal. Biochem.* 169:104–108 (1988)), polypropylene (Polsky-Cynkin et al. *Clin. Chem* 31:1438–1443 (1985)), nylon (Van Ness et al., *Nucl. Acids Res.* 19:3345–3350 (1991)), agarose (Polsky-Cynkin et al., *Clin. Chem.* 31:1438–1443 (1985)), sephacryl (Langdale and Malcolm, *Gene* 36:201–210 (1985)), latex (Wolf et al., *Nucl. Acids Res.* 15:2911–2926 (1987) and paramagnetic beads (Albretsen et al. *Anal. Biochem.* 189:40–50 (1990), Lang et al. *Nucl. Acids Res.* 16:10861–10880 (1988)).

As the polynucleotide synthesis reaction proceeds, the synthesis products produced are bound to a solid support. Preferably, the polynucleotide synthesis reaction is a cyclic amplification reaction. The synthesis product may be released by contacting the bound synthesis products with a suitable releasing enzyme, thereby producing released synthesis products from the immobilized synthesis products. Released polynucleotide synthesis products may be readily transferred from the site of synthesis and subjected to further manipulation or analysis.

Kits for Practice of the Invention

Another aspect of the invention is to provide kits for performing the methods of the invention. The kits of the invention comprise one or more of the enzymes or other reagents for use in performing the subject methods. Kits may contain reagents in pre-measured amounts to ensure both precision and accuracy when performing the subject methods. Preferably, kits contain written instructions that describe how to perform the methods of the subject invention. At a minimum, the kits of the invention comprise a restriction endonuclease and either a nucleoside triphosphate with a base analog inhibitory for that restriction endonuclease or a thermostable DNA polymerase suitable for use in a cyclic amplification reaction. The restriction endonuclease in the kit may be a type IIS restriction endonuclease. In addition, to these embodiments, the kits of the invention may further comprise one or more of the following components: concentrated reaction buffer, DNA ligase, nucleoside triphosphates, mixtures of nucleoside triphosphates in equimolar amounts, nucleoside triphosphates having inhibitory base analogs, mixtures of nucleoside triphosphates and nucleoside triphosphates having inhibitory base analogs, thermostable DNA polymerases, frozen competent cells, positive/negative control templates, control releasable primers, and the like. An example of a kit of the invention is a kit comprising the restriction endonuclease Eam1104I and 5-methylcytosine triphosphate as the inhibitory base analog.

The invention having been described, the following example is offered by way of illustrating the invention and not by way of limitation.

EXAMPLE

Seamless Domain Replacement

Experiments were performed to use the methods of the invention to replace a segment of a plasmid with a corresponding segment of a second plasmid. The experiments did not rely on the use of convenient restriction sites in either plasmid.

Two commercially available plasmids were used for the experiments. The plasmid pBluescripts® II KS contains an alpha complementing fragment of LacZ. The plasmid pWhitescript5.7 is a derivative of pbluescript® II KS (Stratagene) and contains a single point mutation that introduces an ochre stop codon 22 nucleotides downstream from the lacZ ATG. This mutation prevents expression of a functional α-complementing βGal protein, resulting in bacterial colonies that remain white when plated on media supplemented with XGal and IPTG. Exchanging the region that contains the stop codon with that of the parental pBluescript II vector was expected to restore the original blue phenotype of the lacZ gene.

The vector backbone and each domain of interest was PCR amplified in the presence of $^{m5}$dCTP. The primers are given in table I; the underlined segments of the polynucleotide indicate the restriction endonuclease recognition site.

TABLE 1

| (1F) | AGTTA<u>CTCTTC</u>ACCATGATTACGCCAAGCGC | (SEQ ID NO:1) |
| (1R) | AGTTA<u>CTCTTC</u>AGTGAGCGCGCGTAATACG | (SEQ ID NO:2) |
| (2F) | AGTTA<u>CTCTTC</u>ACACTGGCCGTCGTTTTACAACG | (SEQ ID NO:3) |
| (2R) | AGTTA<u>CTCTTC</u>ATGGTCATAGCTGTTTCCTGTG | (SEQ ID NO:4) |

Sense and antisense primers for the plasmid backbone (Primers 2R and 2F) were designed to amplify all but a 190-bp region of the lacZ gene of pWhitescript5.7 that contained the point mutation. The primer pair (1F and 1R) for the 190-bp domain of interest was designed to amplify the fragment from pBluescript II needed to reconstitute the complete lacZ gene. The sense primer was engineered to lie within the lacZ gene, downstream from the translation start site. The PCR products were digested with Eam1104I and subsequently ligated together in the presence of the restriction enzyme, for details see Lin and Schwartz, *BioTechniques* 12:28–30 (1992); Russek et al., *Cell Mol. Biol. Res.*

36:177–182 (1993); Weiner, M. P., *BioTechniques* 15:502–505 (1993). The negative control reaction received no ligase and did not yield colonies upon transformation.

The domain of interest was prepared by PCR amplification of ng pBluescript II SK+ DNA template in a 50-μl reaction containing 200 μM of each dNTP/2.5μ Taq DNA polymerase/2.5μ TaqExtender™ additive/200 nM of each primer 1F and 1R/20 mM Tris Cl pH 8.5/10 mM KCl/10 mM $(NH_4)_4SO_4$/2 mM $MgCl_2$/0.1 mg/ml BSA/0.1% Triton X-100. The reaction was overlaid with mineral oil and amplified once at 94° C. for 3 min/58° C. for 2 min/72° C. for 3 min/with 9 subsequent cycles at 94° C. for 45s/58° C. for 35s/72° C. for 1 min. 5 additional cycles were performed in the presence of $^{m5}$dCTP by adding a 50 μM solution of 200 μM each dATP, dGTP, dTTP/1 mM $^{m5}$dCTP/2.5μ each Taq DNA polymerase and TaqExtender™ additive (Stratagene, La Jolla, Calif.) in the same buffer. The cycling parameters were kept constant except for the denaturation cycle which was increased to 95° C. for 1.5 min. Modification of the denaturation cycle was required because methylated DNA has a higher melting temperature compared to unmethylated DNA. Subsequently, we determined that the length of the denaturation cycle could be reduced to 45 sec. without compromising the product yield.

The vector backbone was prepared in the same fashion as the domain of interest, except for the following modifications. The extension time was changed from 1 min to 12 min to accommodate the slower processivity of the enzyme. The denaturation time was held constant at 45 sec. The resulting PCR products were phenol: chloroform extracted and ethanol precipitated. Approx. 0.3 pmol of vector and 1 pmol of insert were combined and digested with 24 units of Eam1104I in 1× universal buffer (100 mM KoAc, 25 mM tris acetate pH 7-6, 10 mM MgOAc, 0.5 mM β-mercaptoethanol, 10 μg/ml BSA) 1/10 of the crude digest was ligated for 30 min at 37° C. in a 20 μl reaction containing 50 mM Tris-HCl/10 mM MgCl/10 mM DTT/20 μg BSA per ml/1 mM ATP/8 or 6 units Eam1104I/6 Weiss units T4 DNA ligase.

Competent XL-1 Blue MRF′/*E. coli* cells were transformed with 4 μl of the ligation according to the manufacturer's instructions and plated on ampicillin selection medium supplemented with 100 μM IPTG and 10 μg XGal/ml.

The data showed that 2% of the bacterial colonies remained white, whereas 98% exhibited the blue color that was expected of clones carrying the restored lacZ gene (data not shown). The high percentage of blue colonies suggests that the addition of Eam1104I to the ligation reaction provided a selection for the formation of the desired product. The presence of the restriction endonuclease in the ligation mixture not only maintains unmethylated vector in a linear state, but also re-digests unwanted ligation products and thus contributes to the assembly and maintenance of only accurately joined insert: vector pairings, which results in higher cloning efficiency.

Incorporation by Reference

All patents, patents applications, and publications cited are incorporated herein by reference.

Equivalents

The foregoing written specification is considered to be sufficient to enable one skilled in the art to practice the invention. Indeed, various modifications of the above-described methods for carrying out the invention which are obvious to those skilled in the field of molecular biology or related fields are intended to be within the scope of the following claims.

What is claimed is:

1. A method of producing a polynucleotide of interest, the method comprising:

synthesizing the polynucleotide of interest in a polynucleotide synthesis reaction employing a first releasable primer, whereby a polynucleotide synthesis product comprising at least one methylated inhibitory base analog is produced; and cleaving the polynucleotide synthesis product with Eam1104I, whereby a released synthesis product comprising the polynucleotide of interest and containing at least one methylated inhibitory base analog is produced.

2. The method of claim 1, wherein the methylated inhibitory base analog is 5-methyl-cytosine.

3. A method of producing a polynucleotide of interest, the method comprising:

synthesizing the polynucleotide of interest in a polynucleotide synthesis reaction employing a first releasable primer and a second releasable primer, whereby a polynucleotide synthesis product comprising at least one methylated inhibitory base analog is produced; and cleaving the polynucleotide synthesis product with Eam1104I, whereby a released synthesis product comprising the polynucleotide of interest and at least one methylated inhibitory base analog is produced.

4. The method of claim 3, wherein the methylated inhibitory base analog is 5-methyl-cytosine.

5. A method of constructing a polynucleotide of interest, the method comprising:

synthesizing a first polynucleotide of interest in a first polynucleotide synthesis cyclic amplification reaction employing first and second primers, wherein the first and second primers are releasable primers, whereby a first polynucleotide synthesis product comprising at least one methylated inhibitory base analog is produced;

cleaving the first polynucleotide synthesis product with Eam1104I, whereby a first released synthesis product is produced;

synthesizing a second polynucleotide of interest in a second polynucleotide synthesis cyclic amplification reaction employing third and fourth primers, wherein the third and fourth primers are releasable primers, whereby a second polynucleotide synthesis product is produced;

cleaving the second polynucleotide synthesis product with the releasing enzyme specific for a recognition site of the third releasable primer, whereby a second releasable synthesis product is produced; and ligating the first released synthesis product to the second released synthesis product to produce a ligated product, wherein the ligated product comprises the polynucleotide of interest.

6. The method according to claim 5, wherein at least one inhibitory base analog is present in the second polynucleotide synthesis product.

7. The method according to claim 5, wherein the inhibitory base analog is a methylated analog.

8. The method according to claim 5, wherein the inhibitory base analog is 5-methyl-cytosine.

9. A kit for seamless polynucleotide synthesis comprising Eam1104I.

10. The kit according to claim 9, further comprising 5 methyl-cytosine triphosphate.

* * * * *

SEQUENCE LISTING

```
<160> NUMBER OF SEQ ID NOS: 4

<210> SEQ ID NO: 1
<211> LENGTH: 31
<212> TYPE: DNA
<213> ORGANISM: Unknown
<220> FEATURE:
<223> OTHER INFORMATION: Description of Unknown Organism: primer for
      amplification and replication

<400> SEQUENCE: 1
agttactctt caccatgatt acgccaagcg c                                        31

<210> SEQ ID NO: 2
<211> LENGTH: 30
<212> TYPE: DNA
<213> ORGANISM: Unknown
<220> FEATURE:
<223> OTHER INFORMATION: Description of Unknown Organism: primer for
      amplification and replication

<400> SEQUENCE: 2
agttactctt cagtgagcgc gcgtaatacg                                          30

<210> SEQ ID NO: 3
<211> LENGTH: 34
<212> TYPE: DNA
<213> ORGANISM: Unknown
```

```
<220> FEATURE:
<223> OTHER INFORMATION: Description of Unknown Organism: primer for
      amplification and replication

<400> SEQUENCE: 3
agttactctt cacactggcc gtcgttttac aacg                              34

<210> SEQ ID NO: 4
<211> LENGTH: 33
<212> TYPE: DNA
<213> ORGANISM: Unknown
<220> FEATURE:
<223> OTHER INFORMATION: Description of Unknown Organism: primer for
      amplification and replication

<400> SEQUENCE: 4
agttactctt catggtcata gctgtttcct gtg                               33
```